(12) United States Patent
James

(10) Patent No.: US 7,022,491 B2
(45) Date of Patent: Apr. 4, 2006

(54) METHOD FOR DETERMINING MOLECULE—MOLECULE INTERACTION ANALYSIS

(76) Inventor: Peter James, Stadsbudsgatan 1 B, Lund S-227 36 (SE)

( * ) Notice: Subject to any disclaimer, the term of this patent is extended or adjusted under 35 U.S.C. 154(b) by 0 days.

(21) Appl. No.: 10/500,431

(22) PCT Filed: Dec. 16, 2002

(86) PCT No.: PCT/EP02/14315

§ 371 (c)(1),
(2), (4) Date: Dec. 27, 2004

(87) PCT Pub. No.: WO03/056342

PCT Pub. Date: Jul. 10, 2003

(65) Prior Publication Data

US 2005/0095654 A1    May 5, 2005

(30) Foreign Application Priority Data

Dec. 28, 2001 (GB) ................................ 0131014

(51) Int. Cl.
  *G01N 33/53* (2006.01)
  *G01N 33/533* (2006.01)
  *G01N 24/00* (2006.01)
  *G01N 30/02* (2006.01)
  *C07K 1/13* (2006.01)

(52) U.S. Cl. ................ 435/7.8; 435/7.1; 435/7.2; 435/6; 436/544; 436/546; 436/172; 436/824; 436/905; 436/161; 436/173; 436/94; 530/405; 530/412

(58) Field of Classification Search ........... 435/7.8, 435/6, 7.1, 7.2; 436/544, 546, 824, 905, 436/161, 173, 94, 172; 530/405, 412
See application file for complete search history.

(56) References Cited

U.S. PATENT DOCUMENTS 4,487,838 A    12/1984    Hynes et al.

FOREIGN PATENT DOCUMENTS

EP        0 778 280        1/2003
WO      WO 00/02893      1/2000

OTHER PUBLICATIONS

Blackstock, W. P., et al., "Proteomics: quantitative and physical mapping of cellular proteins" Trends in Biotechnology, Elsevier, Amsterdam, NL vol. 17, No. 3, Mar. 1999 pp. 121-127.

Oatis, Jr., J. E., et al., "Synthesis and Photochemistry of Two Cleavable Heterobifunctional Benzophenone Protein Crosslinkers" Tetrahedron Letters, Elsevier Sciences, Ltd. vol. 39, No. 13, 1998 pp. 1665-1668.

*Primary Examiner*—Mary E. Ceperley
*Assistant Examiner*—Shafiqul Haq
(74) *Attorney, Agent, or Firm*—Yonggang Ji

(57) ABSTRACT

The invention relates to a method for monitoring interactions to a target biomolecule comprising the steps of: providing a biomolecule of interest having specificity for the target biomolecule; binding the biomolecule of interest to at least one type of linker molecule comprising a unique mass marker part; introducing the biomolecule of interest to a cell; binding the linker to the target biomolecule; cleaving the linker molecule, thereby leaving the photoactivatable part and the mass marker part bound to the target; analysing the target biomolecule, thereby detecting the unique mass marker part. The detection can be carried out by MS in a parent ion scanning mode, thereby allowing study of the interaction between the biomolecule of interest and the target biomolecule.

25 Claims, 6 Drawing Sheets

METHOD FOR DETERMINING MOLECULE—MOLECULE INTERACTION ANALYSIS

This application is a filing under 35 U.S.C. § 371 and claims priority to international patent application number PCT/EP02/14315 filed Dec. 16, 2002, published on Jul. 10, 2003 as WO 03/056342 and also claims priority to patent application number 0131014.3 filed in Great Britain on Dec. 28, 2001; the disclosures of which are incorporated herein by reference in their entireties.

TECHNICAL FIELD

The invention relates to a method for labelling and analysing molecule-molecule interactions, preferably by mass spectroscopy. Furthermore, the invention relates to a kit for use in the method.

BACKGROUND

The success of the genome projects has resulted in the identification of a vast number of open reading frames (ORFs), which potentially code for proteins. The main problem is now to assign functions to the forty to sixty percent of the ORFs in a genome for which no function can be allocated. Two analytical chemical approaches to this can be identified: transcriptomics and proteomics. Transcriptomics analyses the expression levels of the various mRNA species being transcribed using either a 'gene-chip' or a SAGE approach. This is useful for identifying under which conditions a particular protein is being expressed but provides little direct information as to function. Proteomics, the direct quantitation and analysis of expressed proteins, provides a more direct approach to function definition. Proteomics can be divided into two areas: Expression Proteomics attempts to define all the proteins being expressed in a cell and their post-translational modifications and how these change under various conditions. Cell-Map Proteomics attempts to define the subcellular location of a protein and with which other proteins it is interacting. It is this field which the inventors wish to address in this grant application.

Traditionally, protein-protein interactions have been analysed by the isolation of protein complexes by 'soft' non-denaturing physico-chemical methods such as centrifugation or affinity based isolations. This approach has been facilitated by the use of mass spectrometry to analyse the purified protein complexes either as mixtures or after separation by SDS-PAGE. The method suffers from several drawbacks, the main one being the stability of the complex under the conditions of purification and a lack of a general purification approach to allow a systematic analysis of many proteins. The latter problem has been successfully addressed by the development of the TAP procedure by the group of Bernard Seraphin at EMBL (Rigaut et al., Nat Biotechnol 1999 October; 17(10): 1030–2 and Puig et al., Methods 2001 July; 24(3): 218–29). ORFs are modified so that the proteins they encode contain two affinity purification (TAP) tags, which allow the labelled protein to be rapidly purified to homogeneity. The resulting complex is then analysed by mass spectrometry to identify the co-purifying proteins.

An alternative approach to protein-protein interaction analysis has been the development of the yeast and bacterial two- and three-hybrid systems (Fromont-Racine et al., Nat Genet 1997 July; 16(3): 277–82 and Uetz et al., Nature 10 Feb. 2000; 403(6770): 623–7). This has allowed genome-wide scans of all protein-protein interactions in a genome to be carried out. The main drawback here is that transient interactions and those induced by ligands or phosphorylation are not amenable to analysis by this method. The TAP purification and two-hybrid system methods do not allow one to define which protein is interacting with which other protein in the complex and which parts of the two proteins are involved in this interaction.

EP 0 778 280 (Isis Innovation Limited) relates to a reagent for use in biological and chemical analyses. More specifically, the reagent is comprised of at least two analyte groups linked to a tag comprising one or more reporter groups adapted for detection by mass spectrometry (MS). More specifically, the group for MS detection is a tertiary amino group, which increases sensitivity and which does not allow generation of a specific ion for parent ion scanning. Hence, the disclosed reagent cannot be used in parent ion scattering.

Further, WO 00/02893 (Brax Group Limited) relates to a method of characterising an analyte, which method comprises to provide a compound in which the analyte is attached by a cleavable linker to a mass marker relatable to the analyte; to cleave the mass marker from the analyte; and to identify the mass marker. More specifically, the marker is a metal ion-binding moiety. To achieve a high ionisation, the labels disclosed are pre-ionised.

Accordingly, there is a need for alternative methods in the field of proteomics, solving the posed problems and providing new opportunities to gain more detailed information about molecule-molecule interactions.

SUMMARY OF THE INVENTION

One object of the invention is to provide a method meeting the demands on this point. This and other objects are accomplished by a method for labelling a target biomolecule, interacting with a specific biomolecule of interest, also denoted bait, as disclosed in the first claim of the application. Hereby, the target biomolecule is labelled with a unique mass marker, which preferably is detected by mass spectroscopy, using a parent ion scanning mode. The method has a wide applicability, allowing the study of interactions between several types of biomolecules. A specific object of the invention is to provide means for the study of interactions between proteins and small molecules or ligands. A further object of the invention is to provide a kit for use in the method of the invention.

An advantage with the present invention is that it enables focus on transient and low affinity protein-protein (ligand) interactions that the conventional methods described in the introduction do not allow. The inventor discloses herein a mass spectrometric approach that will enable one to pick out the 'target protein' to which the labelled bait protein has been crosslinked. The protein of interest, the bait is modified with a chemical or photoactivatable linker either in situ or externally and then introduced into the cells. The bait can then be cross-linked by photolysis to the target under defined conditions. The cell is then lysed and the crosslinker cleaved to leave a unique chemical label (the mass marker) on the target, which allows it to be rapidly identified by 'parent ion' scanning in a mass spectrometer. The method 'mass marker transfer' is applicable not only to protein-protein interaction mapping but also to determining the targets of small organic (or inorganic) molecules (ligands) in the cell. This approach has the advantage in that it not only enables one to identify the interacting partner but also to determine the domain on the protein responsible for the interaction. The method is ideally suited to the analysis of rapid transient interactions such as those that occur in signalling cascades as well as for the identification of receptors for small molecules such as drugs or signalling metabolites.

Other objects and further advantages of the present invention will appear from the detailed disclosure that follows.

DEFINITIONS

Figure 1:
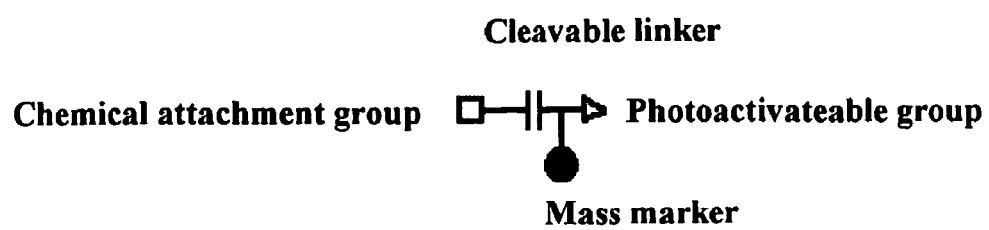
FIG. 1 shows the general form of linker molecule of the invention.

By "a target biomolecule" is in this context meant the molecule which is desired to find and analyse.

By the term "interacting biomolecule" is meant a biomolecule that can attach to a target by chemical binding, ionic interaction, hydrogen bonding, affinity adsorption or any other principle that couple one biomolecule to another. The interaction may well be based on more than one of the above mentioned principles.

By "a biomolecule of interest", or "bait" is meant a molecule potentially having specificity for the target biomolecule. It is the interaction between the biomolecule of interest and the target biomolecule that is desired to monitor by the invention.

By "linker molecule" is meant a molecule, which is used for cross-linking the biomolecule of interest and the target biomolecule. The linker molecule comprises "an attachment part" for binding to the biomolecule of interest, "a photoactivatable part", which has the ability to be activated and thereby be able to bind to the target biomolecule, "a cleavable part", which may be cleaved during the analysis step of the invention, and "a mass marker part" which provides a unique mass marker for the subsequent analysis.

DETAILED DESCRIPTION OF THE INVENTIONS

A first aspect of the invention is a method for identifying an interacting target biomolecule to a biomolecule of interest comprising the steps of:

(a) providing a biomolecule of interest having specificity for the target;

(b) binding the biomolecule of interest to at least one type of linker molecule, the linker molecule comprising at least one attachment part for binding to the biomolecule of interest, one cleavable part, one mass marker part and one photoactivatable part, for binding to the target;

(c) contacting the biomolecule of interest with a cell or a cell extract;

(d) exposing the cell to photolysis, whereby the photoactivatable part binds to the target;

(e) cleaving the linker molecule, thereby leaving the photoactivatable part and the mass marker part bound to the target;

(f) analysing the product of step (e), thereby detecting the mass marker part, thus identifying the interacting target biomolecule to the biomolecule of interest.

The target biomolecule is a polypeptide, a protein, a nucleotide, a small molecule, or any other biomolecule, such as a fatty acid or a carbohydrate. Preferably, the target biomolecule is a protein.

As a first step of the invention the biomolecule of interest is provided. Preferably, the biomolecule of interest is provided in a concentration as close as possible to that as is naturally found in the cell type being analysed. The method for isolating the biomolecule of interest depends on the nature of the molecule. For instance, drug molecules may be provided by chemical synthesis, and proteins by expression and purification. The biomolecule of interest is any biomolecule, small molecule or ligand, which potential interaction with another biomolecule is desired to study. Accordingly, if its interaction with a specific target is already known, the present method can be used to determine whether such a target is present in a specific cell. This can for example be used in diagnosis of disease, where the target then is a known marker of a disease condition. Alternatively, various ligands, such as a combinatorial library of peptides, may be tested for their ability to bind specific target known to be present in a cell. This can for example be used in the screening of new drugs or drug candidates. In one embodiment the biomolecule of interest is selected from the group that consists of a polypeptide, a protein, a nucleotide, a small organic or inorganic molecule, a fatty acid and a carbohydrate. Preferably, the biomolecule of interest is a peptide, or a small molecule. In this context, the term "small" is used for molecules sufficiently small for the herein-described use. The minimum size of the biomolecule of interest is what is required for efficient binding. For instance, this may be tried out using a series of different sizes, whereby the best is chosen. The affinity of the biomolecule of interest for the target biomolecule should be sufficiently strong for the binding to last long enough for the herein disclosed purpose, i.e. to enable an identification of a target, and may for example be in the mM to pM range, for example 10 mM to 0.1 pM.

Thereafter, in step b, the biomolecule of interest is bound, preferably by photoactivation under conditions as close to native as possible, to a linker molecule. The linker molecule comprises an attachment part for binding to the biomolecule of interest. In one embodiment, the attachment part of the linker molecule is designed to bind a specific amino acid residue of the biomolecule of interest. In a preferred embodiment, the attachment part is a N-hydroxysuccinimide moiety or a N-maleimide.

Furthermore, the linker molecule comprises a photoactivatable part, for subsequent binding to a target biomolecule, a mass-marker part, for allowing analysis of the target, and a cleavable part, for separation of the target and the agent.

In the next step, step c, the biomolecule of interest is introduced in a cell either by active uptake, such as by pinocytosis, or by permeabilising the cells temporarily, e.g. by digitonin. Alternatively, a cell free system may be used, especially if one or more of the present biomolecules are carbohydrates. Also, the cell may be perforated or in the form of a cell extract. The mixture obtained of biomolecule of interest and cell or cell extract is the allowed a sufficient period of time for the desired binding to occur. In one embodiment where the target biomolecule is a nucleotide, the method also either provides entrance thereof into a nucleus of a cell or alternatively the interacting biomolecule is contacted with a disrupted nucleus.

Alternatively, the experiment may be carried out in cell extracts.

Thereafter, the cell or the cell-free system is exposed to photolysis. The system is preferably kept at constant temperature, and any standard UV lamp is useable. Preferably, a tungsten carbide lamp is favoured after filtering to remove far UV, which is done by passing the light through a 1M copper sulphate solution (path length 1 cm). Hereby, the photoactivatable part of the linker molecule is activated, thereby allowing it to bind to the target biomolecule. In one embodiment, the photoactivatable part is an azide or a benzophenone. Benzophenone may need repeated photoactivations in order to bind to the target. However, if repeated activations are performed, the probability for the benzophenone-part to bind to the target may be as high as 80%.

If the activatable part is a compound that can be activated by chemical means, the activation is provided by adding such a suitable chemical. Chemical activation is well known in the field of biochemistry, and the skilled person can easily choose a suitable combination of chemically activatable part/chemical degrador or cleaver.

One advantage of activating the above discussed part for binding after it has entered the cell is that undesired unspecific binding with other molecules will then be avoided. However, the above discussed part may have been activated to be able to bind a target before being contacted with the cell, as long as the binding to the target is sufficiently specific for the method to be functional.

Furthermore, in order to achieve an adequate degree of binding, i.e. one that lasts throughout the present procedure and one that can withstand the conditions used, wherein normally about 10% binding degree is necessary, target linker molecules having varying lengths may be used in the invention in order to secure that at least some of the linkers bind to the target. Moreover, if the linker molecule is very long, it may tend to bind water, thereby limiting its activity for the target. The reason for the linker molecule to be used in varying lengths, is that due to the nature of the method, the site where the linker molecule may bind to the target as well as the parts of the biomolecule of interest and the target biomolecule that interact to one another, are unknown at forehand. Thus, it is desired to provide a linker molecule, which has the ability to bind to the target biomolecule, even though there might be some distance between the binding site to the biomolecule of interest and to the target biomolecule. Moreover, by using linker molecules having varying lengths, information about the naturally occurring interaction between the bait and the target may be provided; i.e. by studying what length of the linker molecule is optimal for binding to the target, information about distances between interacting parts of the target and the bait may be revealed.

As mentioned above, in a specific embodiment, the present biomolecules are nucleotides, in which case the above described linker is tailored to link a nucleotide to another nucleotide, while keeping the feature of being cleavable as described above. Similarly, in alternative embodiments, the biomolecules are carbohydrates, and the linker can link a carbohydrate to another carbohydrate. Especially advantageous embodiments are when the biomolecules i.e. the target and the biomolecule of interest are of different kinds, in which cases the linker is capable of providing e.g. nucleotide-protein crosslinking, protein-carbohydrate etc.

Subsequently, in step (e), the linker molecule is cleaved, thereby releasing the biomolecule of interest from the target biomolecule, and leaving the part of the linker molecule comprising the mass marker bound to the target. The cleaving of the cleavable part of the linker molecule may be performed by chemical means. In one embodiment the cleavable part is cleaved by an oxidising agent or by a base agent. More specifically, the cleavable part may be a geminal diol or an ester linkage, which can be cleaved by mild oxidation with 10 mM periodate, e.g. for 30 minutes at room temperature, or basic conditions, e.g. at a pH>9 for two hours at room temperature, respectively.

Optionally, the product of step (e) of the invention, i.e. the target biomolecule, may be cleaved by enzymatic means either separately or combined with the above-discussed chemical means. For instance, the digestion may be performed by using cyanogen bromide and/or trypsin. The cleaving can comprise an enzymatic digestion, such as with an enzyme, such as a protease (e.g. trypsin, V8 protease, such as *Staphylococcus aureus* V8 protease, LysC, AspN etc) or a glycosidase, or a chemical digestion, such as with cyanogen bromide. However, as regards membrane and/or membrane associated proteins, due to their compact structure and tendency to aggregate when denatured, conventional enzyme digestions can be found to be inefficient. In one embodiment which is especially advantageous for membrane and/or membrane proteins, the cleaving in step (b) is an enzymatic digestion preceded by addition of a digestive chemical, such as cyanogen bromide. More specifically, the present inventors have used a scheme wherein the proteins are first digested with cyanogen bromide in a powerful solvent, such as 70% formic or trifluoroacetic acid, with or without hexafluoropropanol. This generates medium sized fragments which can be readily solubilised by a conventional method, e.g. in 1% SDS, before dilution to about 0.01% and digestion with LysC protease. In an alternative embodiment, acid-based cleavages are used, as reported by the group of Tsugita (Kamo et al. 1998 and Kawakami et al. 1997). Thus, in one embodiment, the cleaving in step (b) is a serine/threonine cleavage with a fluorinated acid. In a detailed embodiment, site specific cleavage at serine and threonine is carried out in peptides and proteins with S-ethyltrifluorothioacetate vapour as well as at aspartic acid residues by exposure to 0.2% heptafluorobutyric acid vapour at 90° C. Such a serine/threonine cleavage method is advantageous, since Ser and especially Thr are found often in transmembrane segments. In summary, the skilled in this field can select the most appropriate method to cleave the proteins in the sample depending on factors such as the source of the sample, the purpose of the labelling etc. The digested proteins obtained according to the present invention are much easier to handle since physicochemically they are much simpler. Thus, an essential advantage with the present invention is that the separation of peptides obtained according to the invention can be selected to pick out virtually any one or ones of those present in the original sample as proteins, since the present digestion will be essentially total. Accordingly, in the step of separation and the subsequent labelling, any one of all possible peptides, i.e. fragments of proteins, can be treated, even cysteine-containing peptides, as will be discussed in more detail below. This should be compared to the prior art methods, wherein proteins can be hidden or concealed due e.g. to self-aggregation. Prior methods required the separation of intact proteins and could not deal with peptide digests without losing the quantation aspect. The present method of cleavage provides homogenous peptides, which can be separated without the problems associated with proteins have multiple domains (hydrophobic and hydrophilic) which cause them to run at multiple positions. The present digestion method also allows the analysis of proteins that are otherwise completely insoluble or are parts of large complexes, which cannot be easily separated, especially cytoskeletal aggregates or proteoglycans.

The purpose of the next step of the method, step (f), is to separate and analyse the target biomolecule with its bound mass marker part. Normally, this is performed by coupling an initial multidimensional HPLC to a mass spectrometer (MS). In one embodiment of the present method, the separation is by multi-dimensional chromatography. In another embodiment of the present method, standard reverse phase HPLC is used to separate the majority of the peptides. In a specific embodiment which is efficient if it is desired to get the most hydrophobic peptides, a hydrophilic interaction chromatography (HILIC) approach is used. Alternatively, a first dimension separation can be carried out by ion exchange in the presence of a detergent such as octylglucoside as demonstrated previously (James P, Inui M, Tada M, Chiesi M, Carafoli E. The nature and site of phospholamban regulation of the Ca2+ pump of sarcoplasmic reticulum. Nature. 2 Nov. 1989; 342 (6245):90–2; James, P., Quadroni, M, Carafoli, E., and Gonnet, G. (1993) *Biochem. Biophys. Res. Comm.* 195, 58–64. Protein identification by mass profile fingerprinting). The detergent is then easily removed prior to RP-HPLC-MS analysis by using a normal phase pre-column.

Moreover, in a preferred embodiment of the invention, the mass marker part has the ability to fragment during the analysis step. For example, the mass marker part is thioethyl-pyridine. Hereby, a unique mass marker is achieved, which may easily be detected by mass spectrometry. In a preferred embodiment, the MS is in a parent ion scanning mode (Anal Chem 1 Feb. 1996; 68(3):527–33. Parent ion scans of unseparated peptide mixtures. Wilm M, Neubauer G, Mann M. and Carr et al. 1993, Anal Chem 1 Apr. 1993; 65(7):877–84 Collisional fragmentation of glycopeptides by electrospray ionisation LC/MS and LC/MS/MS: methods for selective detection of glycopeptides in protein digests. Huddleston M J, Bean M F, Carr S A) (also described in the example section), wherein target biomolecules comprising the thioethyl-pyridine mass marker easily are detected at 106 m/z. Furthermore, in a preferred embodiment the MS operates in a data-dependent mode, thereby switching from parent ion to daughter ion scanning mode when a target biomolecule containing the marker is detected.

In yet another embodiment, the present method comprises the method described above, which further comprises the step of identifying the amino acid sequence of at least one of the labelled peptides.

In one embodiment, amino acid sequence identification step is by mass spectral analysis using an ion trap spectrometer or a quadrupole time of flight (TOF) instrument. However, as is realised by the skilled in this field, any MS instrument capable of carrying out and measuring peptide fragmentation spectra can be used to this end.

Moreover, the amino acid identification may be followed by a data base search, in order to find homologues, or other relevant information, to the identified sequence. This may be done in order to assign a probable function for the identified sequence.

In yet another embodiment, the linker molecule may comprise a fluorescent protein tag, in order to make it possible to determine its location in the cell, to which it is introduced. Furthermore, the linker molecule may comprise a signal tag, directing it to a specific location or compartment of a cell.

Figure 2:
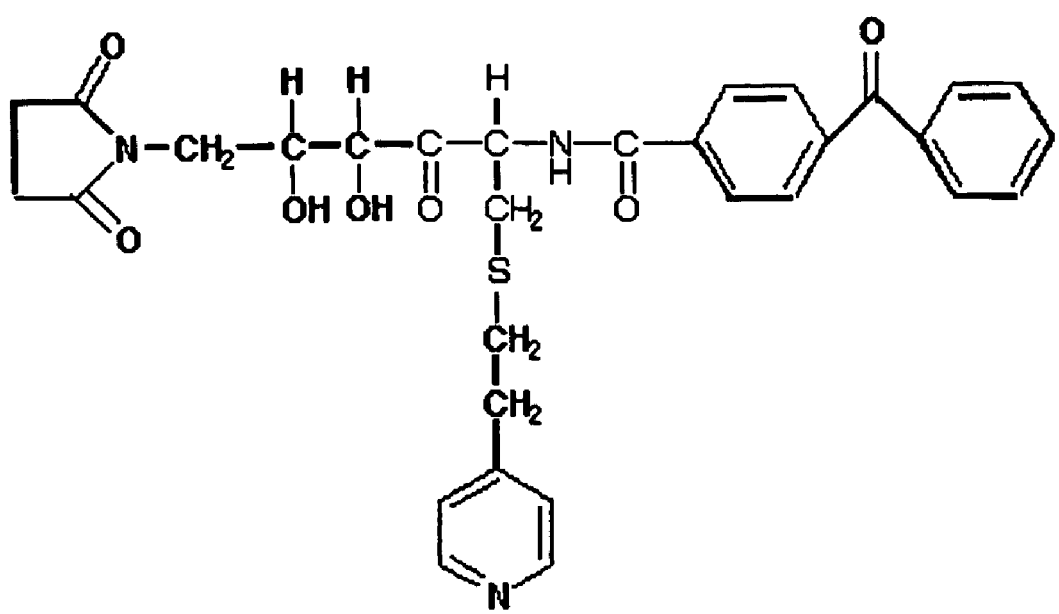
FIG. 2 shows the chemical structure of a specific linker of the invention.

Another aspect of the invention is a linker molecule, which is especially suitable for use in the method of the invention for cross-linking the biomolecule of interest and the target biomolecule. One can envision a wide range of possible crosslinkers that could be useful. FIG. 1 shows the principal functional parts of such a molecule. Each position can be tailored to meet a variety of needs; the chemical attachment group could be an N-hydroxysuccinimide moiety for modification of lysine residues or an N-maleimide for cysteine labelling. The cleavable group could be a geminal diol for cleavage by oxidising agents or an ester linkage for base cleavage. Similarly the photoactivatable group could be an azide for rapid labelling or a benzophenone for high efficiency crosslinking. However, the mass transfer marker that will be used in all cases however will preferably be thioethylpyridine. The thioether bond is chemically extremely stable however it fragments readily under standard low energy MS/MS conditions in a triple quadrupole mass spectrometer. The group leaves as a positively charged ion with m/z of 106. This mass does not correspond to any standard fragment found during low energy fragmentation of peptides and thus provides a unique marker or tag for the peptide to which it is attached. In one preferred embodiment, the linker molecule is 2-benzophenon-4-yl-carbonylamino-4,5-dihydroxy-6-(N-succinimidyl)-1-(4-pyridylethylthio)-3-n-hexanone (FIG. 2). However, many variants of this linker are possible. It should comprise the attachment part, the cleavable part, the label part and the photoactivatable part, but they should mostly be seen as functional parts, and must not necessarily be structurally distinguished from each other. The core part of the linker molecule is its ability to render a unique mass marker in the gas phase, making it suitable for parent ion scanning, which feature is a result of the thioether bridge.

One essential advantage of this approach compared to standard cross-linking methods using radioactive transfer markers such as the Denny-Jaffe reagent (Denny, J. B. and G. Blobel (1984). "125I-labeled crosslinking reagent that is hydrophilic, photoactivatable, and cleavable through an azo-linkage." Proc Natl Acad Sci USA 81(17): 5286–90) is that the crosslinked peptide is unequivocally identified during parent ion scanning. Radioactive markers have the problem that the peak of radioactivity occurs in an HPLC fraction together with many other peptides and so multi-dimensional chromatography is necessary. Also the detection of the cross-linked product and the identification by sequencing occur concurrently.

Yet another aspect of the invention is a kit for use in the method of identifying an interacting target biomolecule to a biomolecule of interest according to the present invention, which comprises, in separate compartments, at least one linker molecule, and optionally the biomolecule of interest. Furthermore, the kit may comprise necessary reagents for the different steps of the method of the invention, as discussed above or in the example section. The kit comprises amounts of the reagents, which is sufficient for performing the method of the invention. In addition, the kit can also comprise written instructions for its use.

In one embodiment, the present kit comprises a biomolecule of interest in a suitable buffer, a linker molecule as described above, and a cleaving agent that can cleave a part of the linker under appropriate conditions, each component being present in a separate compartment. In one embodiment, the linker comprises a part that can be photo-activated to enable it to bind to a suitable target, as described above. In an alternative embodiment, said part of the linker that can be activated by chemical means, in which case the kit also comprises a suitable substance for providing such activation. In an advantageous embodiment, the present kit comprises an interacting biomolecule bound to a linker, and optionally a chemical compound capable of activating a part of the linker to enable binding thereof to a target biomolecule.

Still another aspect of the invention is the use of a linker molecule as described above for labelling the target biomolecule in the method of the invention.

DETAILED DESCRIPTION OF THE DRAWINGS

FIG. 1 shows the general form of cross-linker molecule of the invention comprising chemical attachment group, cleavable linker, mass marker and photoactivatable group.

FIG. 2 shows the chemical structure of a specific linker of the invention, namely 2-benzophenon-4-yl-carbonylamino-4,5-dihydroxy-6-(N-succinimidyl)-1-(4-pyridylethylthio)-3-n-hexanone.

Figure 3:
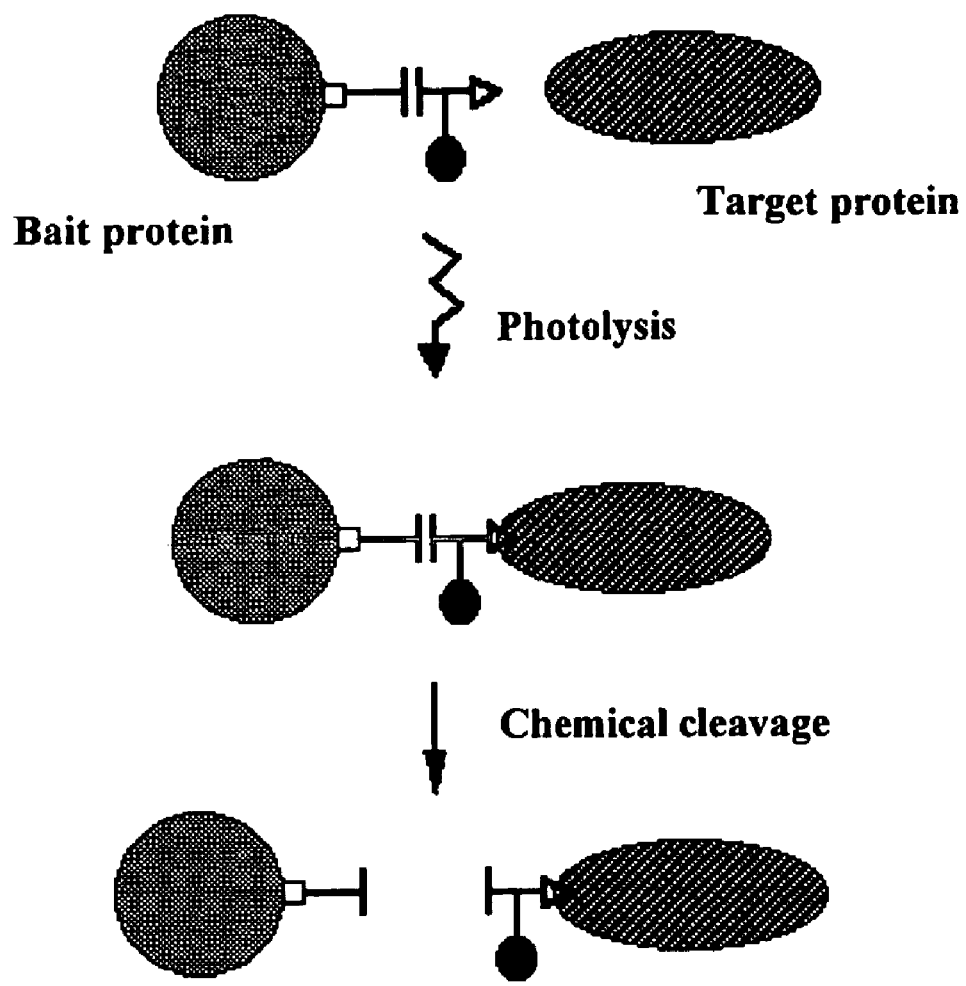
FIG. 3 is a schematic outline of the principle of the mass marker transfer method of the invention.

FIG. 3 is a schematic outline of the principle of the mass marker transfer method of the invention including the steps of photolysis and chemical cleavage.

Figure 4:
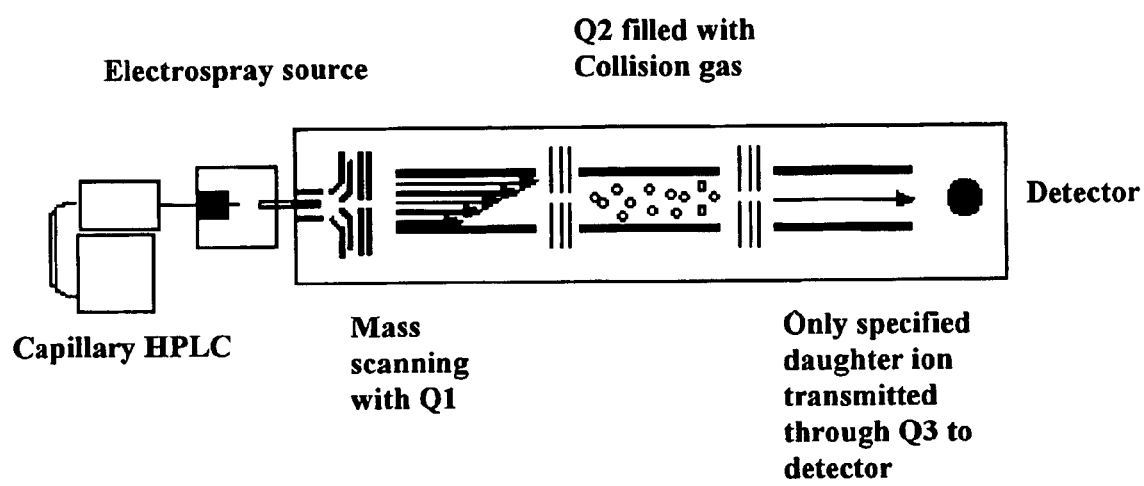
FIG. 4 shows the parent ion scanning principle.

FIG. 4 shows the parent ion scanning principle. Capillary HPLC, electrospray source, a tube with collision gas and detector are shown.

Figure 5:
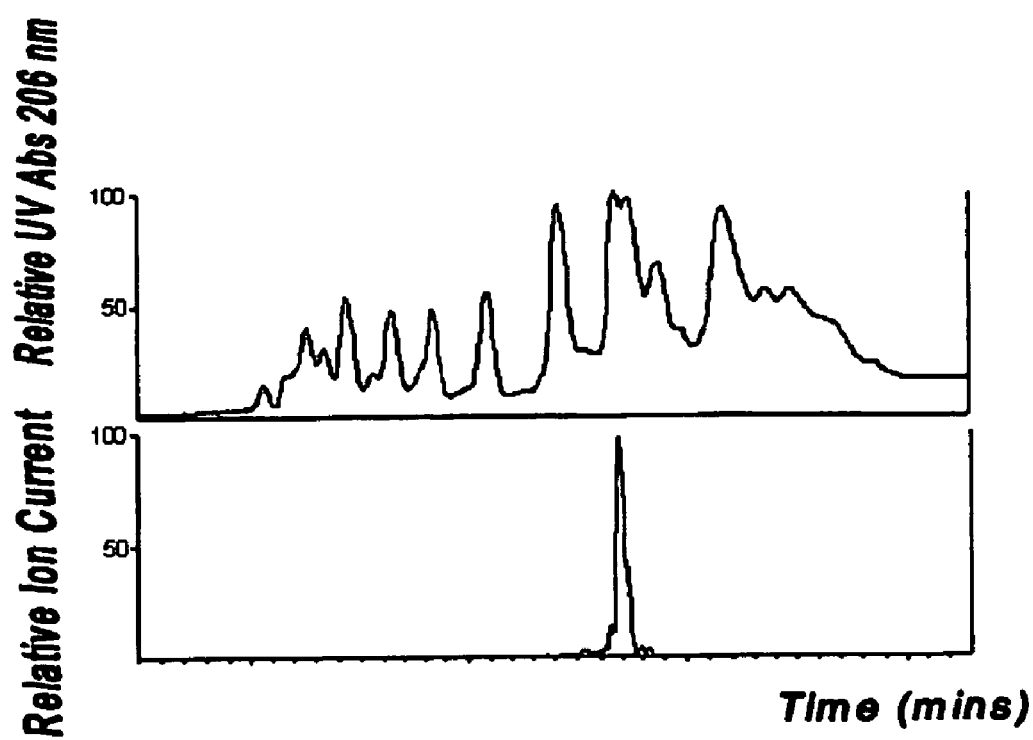
FIG. 5 shows a daughter ion spectrum and HPLC UV vs. RIC trace.

FIG. 5 shows a daughter ion spectrum and HPLC UV vs. RIC trace, with relative ion count/relative UV absorption on the Y-axis and time on the X-axis.

Figure 6:
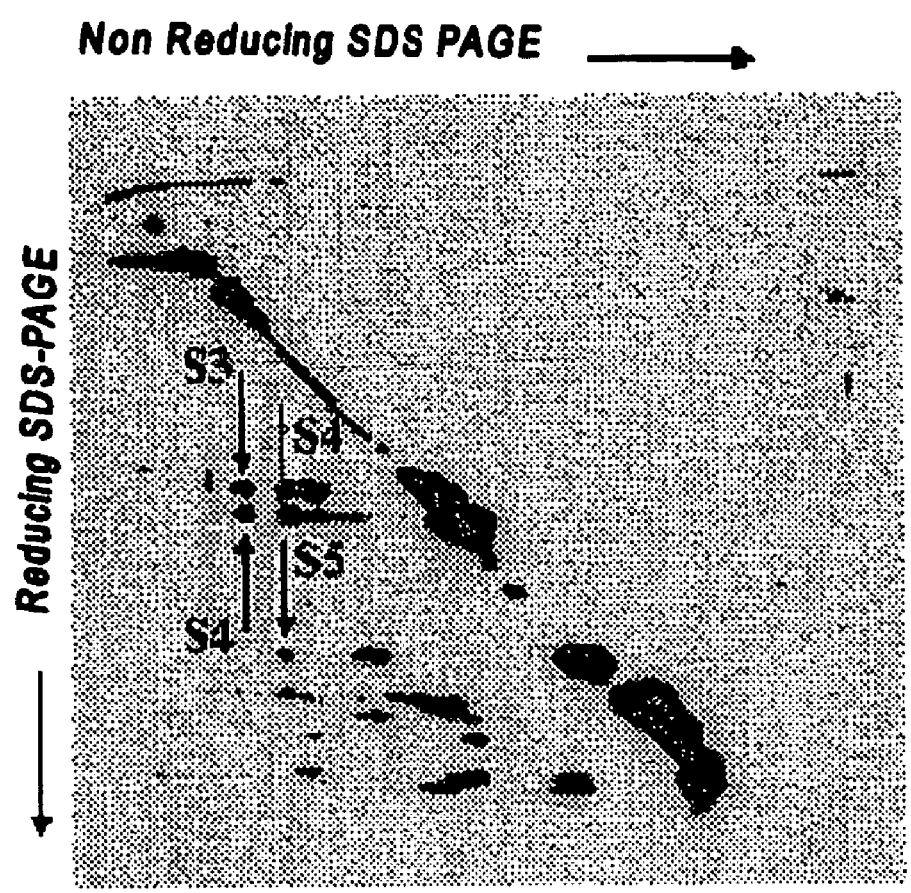
FIG. 6 is a photo of a diagonal gel electrophoresis run.

FIG. 6 is a photo of a diagonal gel electrophoresis run according to conventional procedure.

The invention will now be described with the following examples, which are only intended to be of exemplifying character, and therefore not limiting the scope of the invention in any way. All references given below and elsewhere in the present application are hereby included herein by reference.

Experimental Part

EXAMPLE 1

The Principle of the Method of the Invention

To illustrate the invention, the principle of the method is shown in FIG. 3. The linker is attached to lysine residues on the bait protein. The protein is then introduced to a perforated cell or a cell extract and allowed to equilibrate before photolysis. After crosslinking the proteins are cleaved by oxidisation and the mixture is first digested with cyanogen bromide and then by trypsin.

The complex peptide mixture is then analysed by multidimensional HPLC inter faced by electrospray ionisation to a mass spectrometer operating in parent ion scanning mode as shown diagrammatically in FIG. 4. By operating the mass spectrometer in parent ion scanning mode, only those peptides that give rise to an intense ion at 106 m/z will be detected. The mass spectrometer can be programmed to operate in a data-dependant mode, switching from parent ion to daughter ion scanning mode once a peptide containing the marker is detected. FIG. 5 shows a preliminary experiment that has been carried out to validate the general principle of the approach. A synthetic calmodulin-binding peptide was modified with the crosslinker and photolysed in the presence of calcium and calmodulin. The mixture was then digested with cyanogen bromide followed by trypsin and the peptides separated by HPLC. The UV trace in FIG. 5 shows that the expected number of peptides are generated whereas the parent ion total ion current trace shows that only one peptide has been labelled by the mass marker transfer method.

Initially the inventors will synthesis again the molecule shown in FIG. 2 and later they will extend this to a range of photoactivatable probes specifically tailored to certain types of problem (such as nucleotide-protein crosslinking or protein-carbohydrate for example).

Having synthesised the crosslinker molecule of FIG. 2 (2-benzophenon-4-yl-carbonylamino-4,5-dihydroxy-6-(N-succinimidyl)-1-(4-pyridylethylthio)-3-n-hexanone) it is tested using the calmodulin system mentioned briefly above. Calmodulin is an 18 kDa calcium binding protein involved in calcium signal transduction in many cells. Upon binding calcium it undergoes a conformational change allowing it to bind a specific domain on its target proteins. The structure of calmodulin alone and as a complex with several of its targets has been elucidated both by X-ray crystallography and NMR and hence will allow the inventors to validate the results they obtain from the cross-linking experiments. Calmodulin-binding domains from four different proteins have been synthesised.

EXAMPLE 2

Site-Specific Introduction of Probes into Proteins

In order for the present method to be of general use, one should be able to locate the crosslinker on the bait protein at specific locations, especially if a protein interacts with more that one target. The inventor uses a cell-free translation system that is commercially available, namely the Roche rapid translation system (RTS). The N-maleimide derivative of FIG. 2 is synthesised and attached to cysteine. This in turn can be coupled to a tRNA with a defined codon specificity as described by Josef Brunner's group and more recently that of Peter Schultz. Site-specific incorporation of the crosslinker is rapidly achieved and commonly 100 µg quantities can be prepared overnight. The protein carries two affinity tags and can be rapidly purified. The protein must then be introduced into the cells of interest by either active uptake or by permeabilising the cells temporarily by digitonin. Alternatively the experiment may be carried out in cell extracts. Once the cDNA encoding the protein is correctly engineered into the carrier plasmid, one can rapidly produce mutants by PCR with the codon for the modified tRNA. Thus, tens of proteins modified at different positions can according to the invention be produced within a week once the system is set-up.

EXAMPLE 3

Methods for the Analysis of Large Complexes

If a complex is very large another approach must be taken for the introduction of crosslinkers into the bait proteins. According tot he invention, crosslinkers are introduced in a random fashion by chemical means. A very gentle method of modification for crosslinking was introduced by the group of Traut to map protein-protein interactions in the ribosome. Iminothiolane, a reagent that reacts with lysine residues to give a free sulphydryl group in their place, was used to modify the intact complex under mild conditions. Oxygen was then bubbled into the solution causing neighbouring sulphydryl groups to crosslink to form disulphide bridges. The complex was then separated by diagonal gel electrophoresis, in which the first dimension is non-reducing SDS PAGE and the second is done under reducing conditions. Non-crosslinked proteins appear along the diagonal axis at a position proportional to their mass whereas crosslinked proteins appear as off diagonal vertically separated pairs as shown in FIG. 6. This method can be modified slightly to incorporate a mass marker introduction step between the first and second dimension. Thus, all interacting pairs appearing off-diagonal can be rapidly identified by protein fragment fingerprinting (James, P., Quadroni, M, Carafoli, E., and Gonnet, G. (1993) *Biochem. Biophys. Res. Comm.* 195(1), 58–64. Protein identification by mass profile fingerprinting.) and their sites of interaction can be analysed simultaneously by the parent ion scanning method outlined in FIGS. 4 and 5.

EXAMPLE 4

High Throughput Interaction Domain Mapping

An approach to mapping domain interactions between proteins can be taken which is similar to that used for mapping epitopes (Houghten, R. A. (1985). "General method for the rapid solid-phase synthesis of large numbers of peptides: specificity of antigen-antibody interaction at the level of individual amino acids." Proc Natl Acad Sci USA 82(15): 5131–5.). The inventor synthesises a series of 20 mer peptides which cover the entire sequence of a protein with 10 amino acid overlaps (i.e. 100 peptides are needed for a 100 kDa protein). Each of the peptides will have a crosslinker at its N-terminal and a long cleavable spacer arm at its C-terminal separating it from the supporting resin. The synthesis is carried out by a standard multi-parallel robotic system (e.g. that of Advanced ChemTech amongst many others) in a 96 well plate format. The known target protein, which has been labelled with a fluorescent group, is then added in the appropriate buffer to the wells and allowed to equilibrate. The wells are then washed under progressively more stringent conditions and the fluorescence in each well determined after each round. Finally, the better binding peptides are then re-equilibrated with target protein and photolysed. The binding position of each peptide on the target is then determined and a domain interaction map is constructed. The procedure is then reversed and the bait protein is fluorescently labelled and used to screen the peptides from the target and the binding results are correlated with the first map to exclude non-specific interactions.

What is claimed is:

1. A method for identifying an interacting target biomolecule to a biomolecule of interest comprising the steps of:
    (a) providing a biomolecule of interest having specificity for the target;
    (b) binding the biomolecule of interest to at least one type of linker molecule, the linker molecule including at least one attachment part for binding to the biomolecule of interest, one cleavable part, one mass marker part and one photoactivatable part, for binding to the target;
    (c) contacting the biomolecule of interest with a cell or a cell extract;
    (d) exposing the cell to photolysis, whereby the photoactivatable part binds to the target;
    (e) cleaving the linker molecule or molecules, thereby leaving the photoactivatable part and the mass marker part bound to the target; and
    (f) analysing the product of step (e), thereby detecting the mass marker part, thus identifying the interacting target biomolecule to the biomolecule of interest.

2. The method of claim 1, wherein the biomolecule of interest is a protein or a peptide.

3. The method of claim 1, wherein the target biomolecule is a protein or a peptide.

4. The method of claim 1, wherein the affinity of the biomolecule of interest for the target biomolecule is in the interval of 10 mM to 0.1 pM.

5. The method of claim 1, wherein the attachment part of the linker molecule is designed to bind to a specific amino acid residue of the biomolecule of interest.

6. The method of claim 1, wherein the attachment part of the linker molecule is a N-hydroxysuccinimide moiety or a N-maleimide.

7. The method of claim 1, wherein the cleavable part of the linker molecule is cleaved by chemical means.

8. The method of claim 6, wherein the cleavable part is cleaved by an oxidising agent or by a base agent.

9. The method of claim 1, wherein the cleavable part is a geminal diol or an ester linkage.

10. The method of claim 1, wherein the mass marker part has the ability to fragment during the analysis step.

11. The method of claim 1, wherein the mass marker part is thioethylpyridine.

12. The method of claim 1, wherein at least two different linker molecules are used.

13. The method of claim 1, wherein the photoactivatable part is an azide or a benzophenone.

14. The method of claim 1, wherein the linker molecule is 2-benzophenon-4-yl-carbonylamino-4,5-dihydroxy-6-(N-succinimidyl)-1-(4-pyridylethylthio)-3-n-hexanone.

15. The method of claim 1, wherein the linker molecule further comprises a fluorescent protein tag.

16. The method of claim 1, wherein the linker molecule comprises a tag directing it to a subcellular location.

17. The method of claim 1, wherein the cell of step (c) is perforated, in the form of a cell extract or in a cell-free translation system.

18. The method of claim 1, wherein the photolysis of step (d) is performed by exposing the cell to UV-light.

19. The method of claim 18, wherein the photolysis is repeated at least once.

20. The method of claim 1, wherein the product of step (d) is chemically and/or enzymatically digested.

21. The method of claim 20, wherein the digestion is performed by cyanogen bromide and/or trypsin.

22. The method of claim 1, wherein step (f) is multidimensional HPLC coupled to a mass spectrometer (MS).

23. The method of claim 22, wherein the MS is in a parent ion scanning mode.

24. The method of claim 23, wherein the molecules comprising the marker is detected at 106 m/z.

25. The method of claim 24, wherein the MS operates in a data-dependent mode, thereby switching from parent ion to daughter ion scanning mode when a peptide containing the marker is detected.

* * * * *